US012354730B2

(12) United States Patent
Schwier et al.

(10) Patent No.: US 12,354,730 B2
(45) Date of Patent: Jul. 8, 2025

(54) DETERMINING CHARACTERISTICS OF MUSCLE STRUCTURES USING ARTIFICIAL NEURAL NETWORK

(71) Applicants: SIEMENS HEALTHINEERS AG, Forchheim (DE); New York University, New York, NY (US)

(72) Inventors: Michael Schwier, Hamburg (DE); Bernhard Geiger, Cranbury, NJ (US); Sasa Grbic, Plainsboro, NJ (US); Esther Raithel, Dormitz (DE); Dana Lin, New York, NY (US); Guillaume Chabin, Paris (FR)

(73) Assignees: Siemens Healthineers AG, Forchheim (DE); New York University, New York, NY (US)

( * ) Notice: Subject to any disclaimer, the term of this patent is extended or adjusted under 35 U.S.C. 154(b) by 391 days.

(21) Appl. No.: 17/662,475

(22) Filed: May 9, 2022

(65) Prior Publication Data

US 2022/0392614 A1 Dec. 8, 2022

(30) Foreign Application Priority Data

Jun. 1, 2021 (EP) .................................. 21177272

(51) Int. Cl.
*G16H 30/20* (2018.01)
*G06N 3/04* (2023.01)
*G06N 3/045* (2023.01)
*G06T 7/10* (2017.01)

(52) U.S. Cl.
CPC ............. *G16H 30/20* (2018.01); *G06N 3/045* (2023.01); *G06T 7/10* (2017.01); *G06T 2207/20084* (2013.01)

(58) Field of Classification Search
CPC . G16H 30/20; G06T 7/10; G06T 2207/20084; G06N 3/045
USPC ........................................................ 382/131
See application file for complete search history.

(56) References Cited

U.S. PATENT DOCUMENTS

| 9,792,531 B2 | 10/2017 | Georgescu et al. |
| 10,600,185 B2 | 3/2020 | Yang et al. |
| 2020/0167911 A1* | 5/2020 | Park .......................... G06T 7/11 |
| 2022/0287664 A1* | 9/2022 | Taki ......................... G06T 7/11 |

FOREIGN PATENT DOCUMENTS

| CN | 111681251 A | * | 9/2020 | ........... G06N 3/0454 |
| CN | 112566580 A | * | 3/2021 | ........... A61B 17/142 |

OTHER PUBLICATIONS

Athwal et al., "Rotator cuff tears", American Academy of Orthopaedic Surgeons, 2017, https://orthoinfo.aaos.org/en/diseases-conditions/rotator-cuff-tears, pp. 1-8.
(Continued)

*Primary Examiner* — Quang N Vo (57) ABSTRACT

Techniques of determining a quantification of at least one characteristic of a muscle structure comprising at least one muscle and at least one tendon are disclosed. The quantification of the at least one characteristic of the rotator cuff may be determined by using at least one artificial neural network and based on one or more medical images depicting the muscle structure of a patient.

18 Claims, 5 Drawing Sheets

(56) References Cited

OTHER PUBLICATIONS

Okoroha et al., "Characterization of rotator cuff tears: ultrasound versus magnetic resonance imaging", Orthopedics, 2017, pp. e124-e130.

Morag et al., "MR imaging of rotator cuff injury: what the clinician needs to know," RadioGraphics, 2006, vol. 26, pp. 1045-1065.

IMV (Information for the Decisions Ahead) 2016 MR Market Outlook Report, "MR Procedure Volume and Mix by Type of Procedure", Dec. 2016, pp. IV25-IV26.

Sambandam et al., "Rotator cuff tears: An evidence based approach", World Journal of Orthopedics, 2015, pp. 902-918.

Paloneva et al., "Increasing incidence of rotator cuff repairs—a nationwide registry study in Finland", BMC Musculoskeletal Disorders, 2015, pp. 1-6.

Ensor et al., "The rising incidence of rotator cuff repairs", Journal of Shoulder and Elbow Surgery, 2013, vol. 22, pp. 1628-1632.

Spencer et al., "Interobserver agreement in the classification of rotator cuff tears using magnetic resonance imaging," The American Journal of Sports Medicine, 2008, vol. 36, pp. 99-103.

Ronneberger et al., "U-Net: Convolutional Networks for Biomedical Image Segmentation", MICCAI 2015, pp. 1-8.

Xu et al., "Supervised Action Classifier: Approaching Landmark Detection as Image Partition", MICCAI 2017, pp. 338-346.

Oh et al., "Indications for rotator cuff repair: a systematic review", Clinical Orthopaedics and Related Research, 2007, pp. 52-63.

Goutallier et al., "Influence of cuff muscle fatty degeneration on anatomic and functional outcomes after simple suture of full-thickness tears", Journal of Shoulder and Elbow Surgery, vol. 12, 2003, pp. 550-554.

Gladstone et al., "Fatty infiltration and atrophy of the rotator cuff do not improve after rotator cuff repair and correlate with poor functional outcome", The American Journal of Sports Medicine, 2007, pp. 719-728.

Slabaugh et al., "Interobserver and intraobserver reliability of the Goutallier classification using magnetic resonance imaging: proposal of a simplified classification system to increase reliability", The American Journal of Sports Medicine, 2012, vol. 8, pp. 1728-1734.

Fuchs et al., "Fatty degeneration of the muscles of the rotator cuff: assessment by computed tomography versus magnetic resonance imaging", Journal of Shoulder and Elbow Surgery, 1999, vol. 8, pp. 599-605.

Nozaki et al., "Predicting retear after repair of full-thickness rotator cuff tear: two-point Dixon MR imaging quantification of fatty muscle degeneration-initial experience with 1-year follow-up", Radiology, 2016, pp. 500-509.

Yang et al., "Automatic liver segmentation using an adversarial image-to-image network", International Conference on Medical Image Computing and Computer-Assisted Intervention, 2017, pp. 1-9.

He et al., "Deep residual learning for image recognition", Proceedings of the IEEE Conference on Computer Vision and Pattern Recognition, 2016, pp. 1-12.

Jahanifar et al., "Automatic Recognition of the Supraspinatus Tendinopathy from Ultrasound Images using Convolutional Neural Networks", Cornell University Library, 2020, pp. 1-28.

Zhang et al., "A Survey on Deep Learning of Small Sample in Biomedical Image Analysis", Cornell University Library, 2019, pp. 1-23.

Kim et al., "Development of an automatic muscle atrophy measuring algorithm to calculate the ratio of supraspinatus in supraspinous fossa using deep learning", Computer Methods and Programs in Biomedicine, 2019, vol. 182, pp. 1-10.

Weber et al., "Deep learning convolutional nearal networks for the automatic quantification of muscle fat infiltration following whiplash injury", Scientific Reports, 2019, vol. 9, pp. 1-8.

Kim et al., "Ruling out rotator cuff tear in should radiograph series using deep learning: redefining the role of conventional radiograph", European Radiology, 2020, vol. 30, pp. 2843-2852.

Lin et al., "Deep-learning diagnosis of supraspinatus tendon tears: comparison of multi-sequence versus single sequence input", International Society for Magnetic Resonance in Medicine (ISMRM), 2020, No. 244, pp. 1-5.

Medina et al., "Deep learning method for segmentation of rotator cuff muscles on MR images", Skeletal Radiology, 2021, vol. 50, pp. 683-692.

Qu et al., "Weakly supervised deep nuclei segmentation using points annotation in histopathology images", Proceedings of Machine Learning Research, 2019, vol. 102, pp. 390-400.

\* cited by examiner

DETERMINING CHARACTERISTICS OF MUSCLE STRUCTURES USING ARTIFICIAL NEURAL NETWORK

This application claims priority to European Patent Application No. 21 177 272.8, filed Jun. 1, 2021, the disclosure of which is herein incorporated by reference in its entirety.

TECHNICAL FIELD

Various examples of the disclosure relate to determining characteristics of a muscle structure of a patient, the muscle structure comprising at least one muscle and at least one tendon. Various examples of the disclosure specifically relate to determining, by one or more artificial neural networks, quantification of at least one characteristic of the muscle structure based on one or more medical images depicting the muscle structure of the patient.

BACKGROUND

Muscle tears, especially tendon tears, are a painful pathology. For example, rotator cuff tears are one of the most common causes of shoulder pain, for example, accounting for almost 2 million U.S. doctor visits in 2013. A meta-study estimates an overall prevalence of rotator cuff tears of 20%-30% in asymptomatic individuals and up to 64% in symptomatic individuals. Furthermore, the incidence of surgical treatments for rotator cuff tears is consistently increasing.

Magnetic Resonance Imaging (MRI) is considered the standard of care for muscle and/or tendon tears, e.g., rotator cuff tear, assessment and treatment planning. The upper extremities, i.e. shoulder and arm constitute 11% of all MR procedures. A tear must be measured in two dimensions on different imaging planes. In addition, it has been shown that rotator cuff muscle structures are prone to fatty infiltration and atrophy after rotator cuff trauma such as tendon tears and that severe fatty infiltration and atrophy correlate with poor functional outcome of rotator cuff repair.

Consistent and accurate measurements of tears, especially rotator cuff tears and assessment of degeneration of the rotator cuff muscle structures (e.g., fatty infiltration and atrophy) are imperative and crucial for selecting the best treatment and surgical approach and impact postoperative prognosis and tear recurrence. In routine clinical practice, radiologists scroll through a large number of MR images to detect tears and then either manually measure the tears in the Picture Archiving and Communication System (PACS) or just estimate the size, and/or to classify fatty infiltration based on the Goutallier classification system and describe the degree of muscle atrophy (volume loss).

However, such techniques face certain restrictions and drawbacks. For instance, MR imaging interpretation of suspected rotator cuff tears is complex and time-consuming, requiring the analysis of several image series acquired in different imaging planes. In addition, studies report significant inter-reader but also intra-reader variabilities resulting in moderate reproducibility in tear assessment, such as quantifications of both tear sizes and the amount of fatty degeneration of the rotator cuff muscle structures.

BRIEF SUMMARY OF THE INVENTION

Accordingly, there is a need for advanced techniques which mitigate or overcome the above-identified drawbacks or restrictions. There is a need for advanced techniques of assessment of muscle and/or tendon tears, such as rotator cuff tears.

This need is met by the features of the embodiments described herein.

Hereinafter, techniques of determining at least one characteristic of the muscle structures are disclosed.

As a general rule, the muscle structure can include at least one muscle. The muscle structure may also comprise at least one tendon. The at least one muscle can contract and expand. The at least one tendon can connect the at least one muscle to a bone. Thus, the muscle structure may be surrounding or be arranged adjacently to the bone.

Various characteristics can be determined, such as at least one of the following anatomical characteristics: presence or absence of muscle and/or tendon tears, tear sizes and degeneration grades of muscles of the muscle structure, and especially measuring a size of the muscle and/or tendon tear and assessing degeneration grades of the muscles automatically and precisely.

As a general rule, it would be possible that the at least one characteristic is a classification of a property of the muscle structure into multiple predefined classes. A classification algorithm can be used.

Alternatively or additionally, the at least one characteristic can include a quantification of a property of the muscle structure. Here, it is not required to rely on predefined classes. A regression algorithm can be used.

The at least one characteristic of the muscle structure may be determined by using at least one artificial neural network and based on one or more medical images depicting a muscle structure of a patient.

A computer-implemented method is provided. The method comprises obtaining one or more medical images. The one or more medical images depict a muscle structure of a patient. The muscle structure comprises at least one muscle and optionally at least one tendon. The method further comprises determining at least one characteristic of the muscle structure using at least one artificial neural network.

For example, a quantification of the at least one characteristic could be determined.

For example, the muscle structure could be a rotator cuff muscle structure. The rotator cuff muscle structure comprises multiple muscles, namely: supraspinatus, infraspinatus, teres minor, and subscapularis.

A computer program or a computer-program product or a computer-readable storage medium includes program code is provided. The program code can be loaded and executed by at least one processor. Upon loading and executing the program code, the at least one processor performs a method. The method comprises obtaining one or more medical images. The one or more medical images depict a muscle structure of a patient. The muscle structure comprises at least one muscle and optionally at least one tendon. The method further comprises determining at least one characteristic of the muscle using at least one artificial neural network.

For example, a quantification of the at least one characteristic could be determined.

A system comprising at least one processor and at least one memory is provided. The at least one processor is configured to load program code from the at least one memory. Upon executing the program code, the at least one processor performs a method. The method comprises obtaining one or more medical images. The one or more medical images depict a muscle structure of a patient. The muscle structure comprises at least one muscle and optionally at least one tendon. The method further comprises determining at least one characteristic of the muscle structure using at least one artificial neural network.

For example, a quantification of the at least one characteristic could be determined.

A medical imaging scanner comprising a system is provided. The system comprises at least one processor and at least one memory. The at least one processor is configured to load program code from the at least one memory. Upon executing the program code, the at least one processor performs a method. The method comprises obtaining one or more medical images. The one or more medical images depict a muscle structure of a patient. The muscle comprises a at least one muscle and optionally at least one tendon. The method further comprises determining at least one characteristic of the muscle structure using at least one artificial neural network.

For example, a quantification of the at least one characteristic could be determined.

It is to be understood that the features mentioned above and those yet to be explained below may be used not only in the respective combinations indicated, but also in other combinations or in isolation without departing from the scope of the invention.

DETAILED DESCRIPTION

Some examples of the present disclosure generally provide for a plurality of circuits or other electrical devices. All references to the circuits and other electrical devices and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microcontrollers, a graphics processor unit (GPU), integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, any one or more of the electrical devices may be configured to execute a program code that is embodied in a non-transitory computer readable medium programmed to perform any number of the functions as disclosed.

In the following, embodiments of the invention will be described in detail with reference to the accompanying drawings. It is to be understood that the following description of embodiments is not to be taken in a limiting sense. The scope of the invention is not intended to be limited by the embodiments described hereinafter or by the drawings, which are taken to be illustrative only.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various techniques disclosed herein generally relate to determining one or more characteristics of a muscle structure of a patient. The muscle structure includes at least one muscle and typically at least one tendon. An example of the muscle structure would be the rotator cuff. For instance, one or multiple characteristics of the muscle structure, especially those characterizing tears of the muscle structure, e.g., rotator cuff tears, can be determined. It would be possible that the characteristics of the muscle structure of different patients are determined automatically, accurately, and based on the same criteria to facilitate inter-patient comparison.

For example, it would be possible that a quantification of at least one characteristic is determined. The quantification can pertain to a numerical value defined in a continuous result space.

In other examples, it would be possible to determine a classification of at least one characteristic. Here, a discrete set of predefined classes is available and the result is a pointer to one of these predefined classes.

As a general rule, the muscle structure can include a group of muscles. The muscle structure may be close to any one of the following joints of a human body: ball and socket joints, hinge joints, condyloid joints, pivot joints, gliding joints, saddle joints, etc.

For instance, the at least one characteristic can affect multiple muscles of the muscle structure.

As a further general rule, the tear may comprise a tendon tear, a muscle fiber tear, or a strain of a tendon and/or a muscle fiber.

According to various examples, at least one characteristic of the muscle structure is determined based on data collected via non-invasive diagnosis methods, such as at least one of projection radiography, computed tomography (CT), ultrasound imaging, MRI, or any other kind of medical imaging modalities, i.e., the medical imaging data or images being processed or analyzed in this disclosure may comprise at least one of MRI image data, X-ray image data, computed tomography image data, ultrasound image data, or any other kind of medical image data. In particular, imaging data acquired by these imaging modalities may be fed to at least one trained artificial neural network, and thereby the at least one characteristic is determined by the trained artificial neural network precisely and automatically.

As a general rule, projection radiography imaging data and ultrasound imaging data utilized in this disclosure may respectively comprise images in spatial domain. CT imaging data and MR imaging data may respectively comprise reconstructed images in frequency domain, reconstructed images in spatial domain and etc. The medical imaging data may be 1-D data obtained directly from a corresponding scanner, 2-D reconstructed images, or 3-D reconstructed slices comprising multiple voxels.

According to the disclosure, MR imaging, especially an MRI scanner with a main magnetic field of 3.0 Tesla, is preferred in evaluations of shoulder because of a greater signal-to-noise ratio (SNR) and contrast-to-noise ratio (CNR) offered by higher main magnetic field strengths due to faster acquisition time and thinner slice selection. Standard conventional MR imaging of the shoulder is acquired in three orthogonal planes: axial, coronal-oblique and sagittal-oblique. Various MR scanning protocols may be utilized to perform a scan of shoulders.

As explained above, the muscle structure described in this disclosure may comprise any one or more muscles and one or more tendons. The muscle may be a human muscle and be muscles of other animals, too. Hereinafter, various techniques of this disclosure will be described in detail based on a rotator cuff as an exemplary muscle structure. I.e., the techniques disclosed in this disclosure can be readily applied to other muscles by simply replacing the term "rotator cuff" with specific names of other muscle structures.

Figure 1:
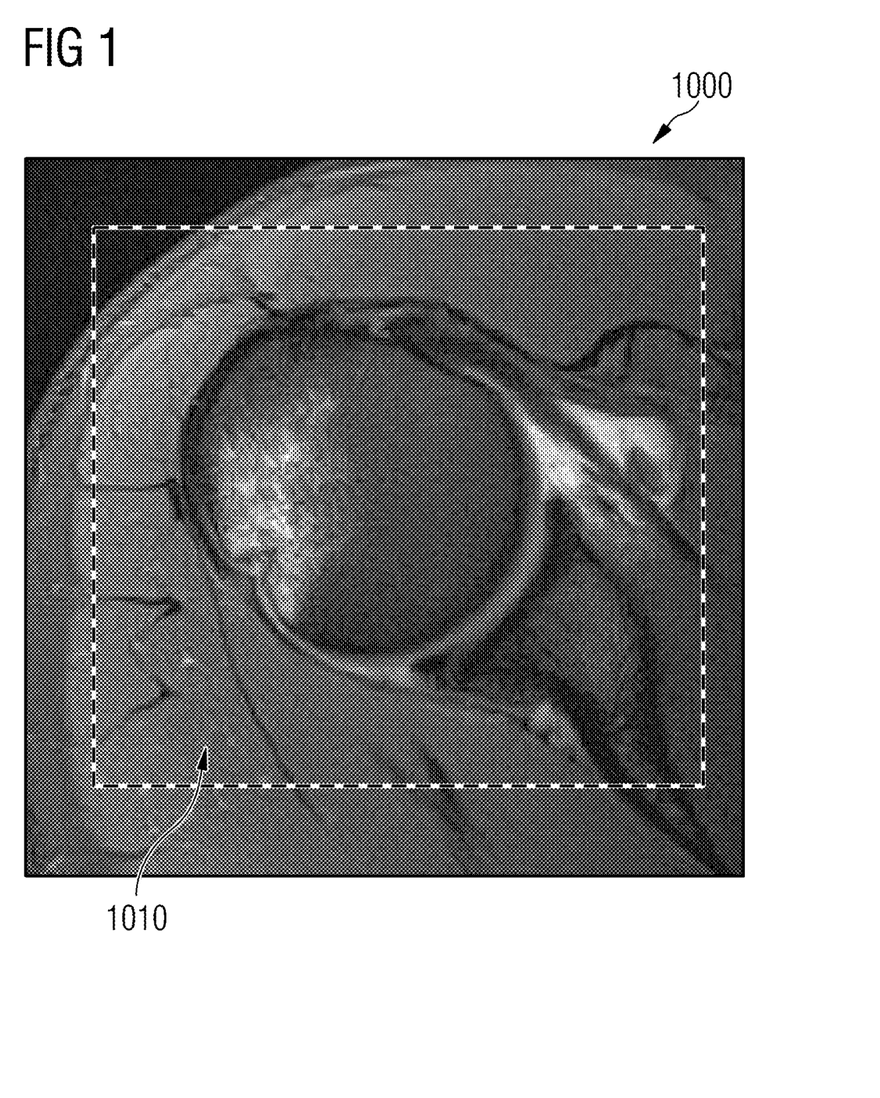
FIG. 1 schematically illustrates an exemplary MRI image acquired in the axial plane.

FIG. 1 schematically illustrates an exemplary MRI image 1000 acquired in the axial plane and depicting the shoulder. The MRI image 1000 may comprise a region of interest (ROI) 1010, i.e., the area inside the dash-lined rectangular. The region of interest 1010 is associated with the rotator cuff. The MRI image 1000 may be cropped to obtain the region of interest 1010 and then only the region of interest 1010 may be fed to the at least one trained artificial neural network to determine the at least one characteristic of the rotator cuff. Similarly, ROIs may be defined on other images obtained via projection radiography, CT, ultrasound imaging, or MRI. Alternatively, ROIs may be also defined on a volume, i.e. 3-D.

According to various examples, the ROI 1010 may be manually determined, e.g., by a clinician.

According to various examples, the ROI 1010 may be determined based on at least one landmark in one or more medical images/slices, such as a rotator cuff tear, a tendon of the rotator cuff. Such a landmark may be detected by using a landmark detection algorithm configured to detect the ROI 1010 in the one or more medical images 1000. Such a landmark detection algorithm may be a machine-learning algorithm.

According to the disclosure, the ROI may comprise at least one tendon comprising rotator cuff muscles, such as the tendon of the Supraspinatus muscle, the tendon of the Infraspinatus muscle, the tendon of the Teres minor muscle or the tendon of the Subscapularis muscle. The following examples may be in the context of a single tendon and/or a single muscle, i.e., the techniques disclosed hereinafter may respectively apply to each individual tendon and/or muscle based on a precise ROI detection. Accordingly, multiple ROIs may be detected in one medical image or slice.

As a further general rule, image pre-processing techniques may be applied to the images or imaging data before they are fed to the at least one trained artificial neural network, for example, cropping images or slices to obtain ROIs, down-sampling to reduce resolutions of images or slices, filtering out noises. Additionally, when the one or more medical images (or imaging data) depicting a rotator cuff of a patient comprises multiple images or slices acquired by one or multiple imaging modalities, registration may be applied to the one or more medical images (or imaging data).

According to the disclosure, the at least one characteristic of the rotator cuff may comprise presence or absence and/or position and/or a type of a tear in a tendon of the rotator cuff. The at least one characteristic may further comprise a classification and optionally a quantification of a muscle atrophy of the rotator cuff. Additionally or alternatively, the at least one characteristic may comprise a classification and optionally a quantification of a fatty infiltration of the rotator cuff. The at least one characteristic may also comprise rotator cuff tear length, width, thickness, and musculotendinous junction position.

According to the disclosure, the Goutallier classification (e.g., See: Slabaugh, Mark A., et al. "Interobserver and intraobserver reliability of the Goutallier classification using magnetic resonance imaging: proposal of a simplified classification system to increase reliability." The American journal of sports medicine 40.8 (2012): 1728-1734.) may be used to quantify the amount of fatty degeneration of the rotator cuff muscles, particularly in the context of rotator cuff tendon tears. Although originally described in shoulder CT, it is applicable and now most commonly used in MRI. It is based mainly on the percentage of atrophy and fatty degeneration of the involved muscle. The grading increases in severity and higher grades correlate with poorer function outcomes following rotator cuff tear surgical repair. The Goutallier classification system may comprise five grades as shown in Table 1.

Figure 2:
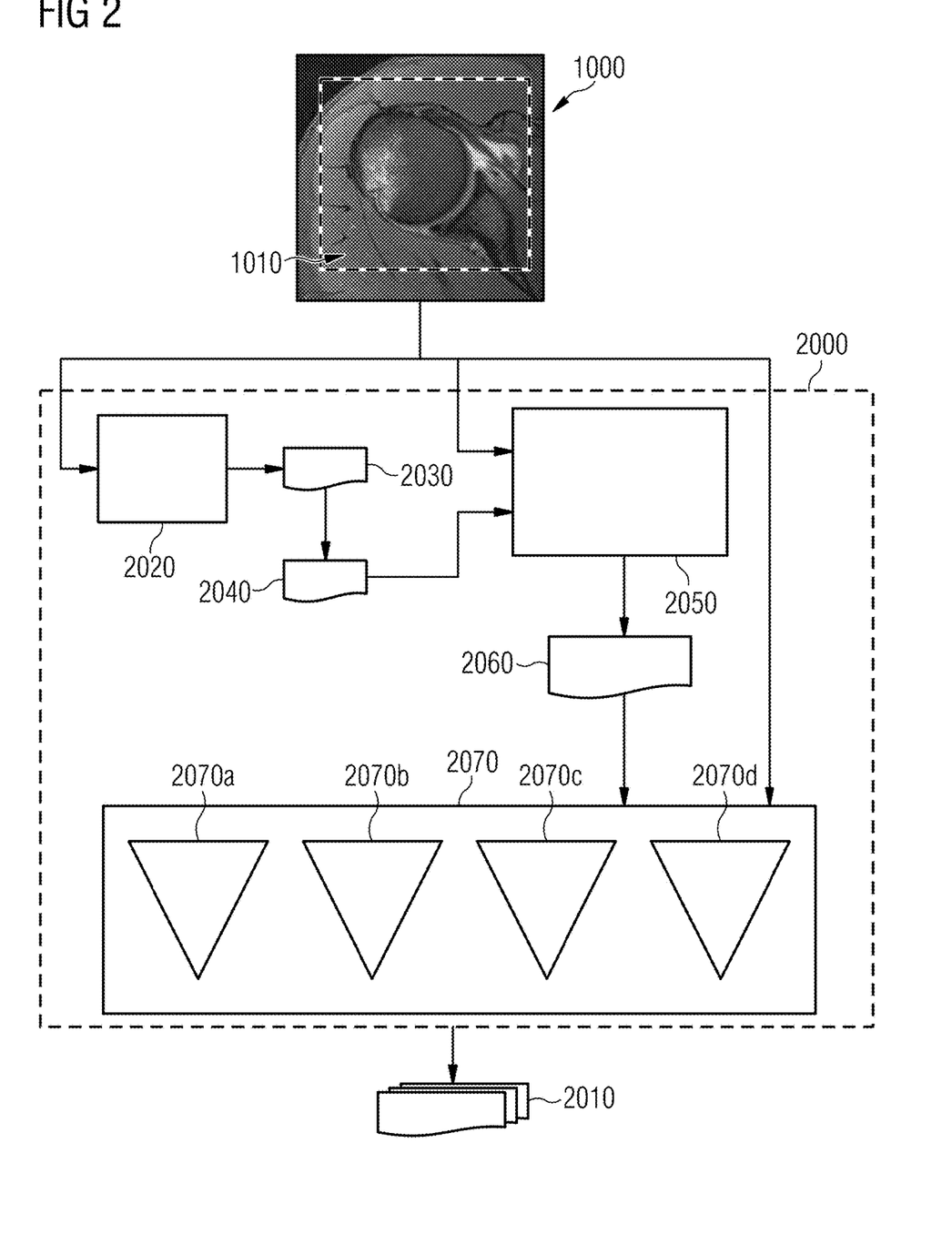
FIG. 2 schematically illustrates details with respect to a system according to various examples.

FIG. 2 schematically illustrates details with respect to a system 2000 according to various examples. The system 2000 may comprise the at least one artificial neural network receiving the one or more medical images 1000 depicting a rotator cuff of a patient as input and outputting, for each of the at least one characteristic, a value indicative of corresponding characteristic. The value indicative of corresponding characteristic may be written in a file 2010. The system 2000 may comprise only one artificial neural network comprising multiple sub-networks.

TABLE 1 various grades of Goutallier classification

| Grade index | Classification criteria |
| --- | --- |
| 0 | normal muscle |
| 1 | some fatty streaks |
| 2 | less than 50% fatty muscle atrophy |
| 3 | 50% fatty muscle atrophy |
| 4 | greater than 50% fatty muscle atrophy |

According to various examples, the system 2000 may comprise a convolutional neural network 2020 which may be configured to perform a pre-segmentation (or coarse segmentation) of the one or more medical images 1000 to determine a pixel probability map 2030, or directly determine a pixel mask 2040. The pixel mask 2040 is obtained by applying a threshold comparison to probability values of the pixel probability map 2030 and selecting a largest contiguous area.

As a general rule, a convolutional neural network may include one or more layers that perform convolutions. Here, a predefined kernel—the weights of which are set during a training phase—is convoluted against input values that are output by a preceding layer.

According to the disclosure, the system 2000 may further comprise a first one 2050 and a second one 2070 of the at least one artificial neural network. The first one 2050 of the at least one artificial neural network may be configured to determine a segmentation 2060 of a region of interest 1010 associated with the rotator cuff in the one or more medical images 1000 based on the pre-segmentation, for instance based on the pixel probability map 2030 or the pixel mask 2040. The segmentation 2060 of the region of interest 1010 determined by the first one 2050 of the at least one artificial neural network may be further based on the one or more medical images 1000 or the ROI 1010. Additionally or alternatively, the segmentation 2060 may comprise a bounding box which may be determined based on the pixel mask 2040. The second one 2070 of the at least one artificial neural network may be configured to determine a value indicative of the at least one characteristic based on the segmentation 2060 of the region of interest 1010 and the one or more medical images 1000.

According to various examples, when the at least one characteristic comprises multiple characteristics, the system 2000 may comprise multiple decoder branches configured to respectively determine the multiple characteristics based on a shared set of latent features determined based on the one or more medical images 1000. For example, the second one 2070 of the at least one artificial neural network may comprise multiple decoder branches 2070a-2070d. Each one of the multiple decoder branches 2070a-2070d may respectively determine at least one distinct characteristic. For instance, the multiple decoder branches 2070a-2070d may determine a size of a tear (e.g., including length, width, and thickness), a percentage of muscle atrophy, a grade of muscle fatty infiltration, and a coordinate of musculotendinous junction position, respectively.

As a general rule, the pixel probability map 2030, the pixel mask 2040, the segmentation 2060, and the bounding box may be 2-D or 3-D.

As a general rule, various kinds and types of artificial neural network can be used as the first one 2050 and the second one 2070 of the at least one artificial neural network and benefit from the techniques described herein, such as convolutional neural networks, reinforcement neural networks, residual neural network, recursive neural network, recurrent neural work, Long short-term memory (LSTM) neural network etc. For instance, it would be possible to use a deep neural network, e.g., a convolutional neural network having one or more convolutional layers performing convolutions between the input data and a kernel, to implement both the first one 2050 and the second one 2070 of the at least one artificial neural network. It would also be possible to use a support vector machine, to give just a few examples. Preferably, the first one 2050 of the at least one artificial neural network may comprise an encoder and a decoder, see, e.g., Ronneberger, Olaf, Philipp Fischer, and Thomas Brox. "U-net: Convolutional networks for biomedical image segmentation." International Conference on Medical image computing and computer-assisted intervention. Springer, Cham, 2015, or Yang, Dong, et al. "Automatic liver segmentation using an adversarial image-to-image network." International Conference on Medical Image Computing and Computer-Assisted Intervention. Springer, Cham, 2017. Preferably, the second one 2070 of the at least one artificial neural network may use deep reinforcement learning approach, see, e.g., Xu, Zhoubing, et al. "Supervised action classifier: Approaching landmark detection as image partitioning." International Conference on Medical Image Computing and Computer-Assisted Intervention. Springer, Cham, 2017. Additionally or alternatively, muscle atrophy and/or muscle fatty infiltration grading in the ROI 1010 may be performed by a residual learning framework, see, e.g., He, Kaiming, et al. "Deep residual learning for image recognition." Proceedings of the IEEE conference on computer vision and pattern recognition. 2016.

According to various examples, the at least one artificial neural network may be implemented by a deep reinforcement learning approach to determine quantification of the tear, such as the tear location (i.e., coordinates of start and end points, respectively), length, width or thickness. Alternatively or optionally, one or more different artificial neural networks may be utilized to implement the at least one artificial neural network for determining classification and optionally the quantification of the muscle atrophy or the fat infiltration.

According to the disclosure, the convolutional neural network 2020 may share the same network architecture as that of the first one 2050 of the at least one artificial neural network. However, the input of the convolutional neural network 2020 may have a lower resolution than that of the first one 2050 of the at least one artificial neural network. The lower resolution can mean that the size of an input vector is smaller; thus, fewer spatial points are sampled by the input vector.

According to various examples, the medical images 1000 or the ROI 1010 fed to the first one 2050 and/or second one 2060 of the at least one artificial neural network also have a lower resolution than that of the original medical images, for example, medical images acquired by a medical imaging scanner, to reduce the computational burden.

According to the disclosure, various training methods of artificial neural networks may be applied to train the at least one artificial neural network, such as supervised learning, un-supervised learning, semi-supervised learning, reinforce learning and etc.

For example, the convolutional neural network 2020, the first one 2050 and the second one 2070 of the at least one artificial neural network may be trained separately using different sets of training data based on supervised learning techniques. Each training process can include determining a loss value based on a comparison between a prediction of the respective one 2050, 2070 of the at least one artificial neural network and a ground truth. A loss function can provide the loss value by performing the comparison. Based on the loss value, it is then possible to adjust the weights of the artificial neural networks. Here, an optimization algorithm, e.g., gradient descent, can be employed. Backpropagation can be an alternative.

Each set of the training data generally comprises one or more training medical images and a set of ground truth in which information relating to the region of interest 1010 is indicated. For example, the set of training data for the convolutional neural network 2020 may comprise annotated pixel probability maps or annotated pixel masks, the set of training data for the first one 2050 of the at least one artificial neural network may comprise annotated segmentation of the region of interest 1010, and the set of training data for the second one 2070 of the at least one artificial neural network may comprise clinical or real values quantifying corresponding characteristic of the rotator cuff. These labels could be assigned by domain experts, e.g., clinicians. Alternatively, the one or more training medical images for the convolutional neural network 2020, the first one 2050 and the second one 2070 of the at least one artificial neural network may be identical.

On the other hand, the convolutional neural network 2020, the first one 2050 and the second one 2070 of the at least one artificial neural network may be trained jointly, i.e., the three neural networks may be regarded as a whole and parameter values of the three (sub) neural networks are updated together by using, for example, back propagation in a joint optimization process based on a common loss value. This corresponds to end-to-end training.

Employing neural networks trained using appropriate sets of training data provide a robust way of processing the medical image data. Neural networks may deal with complex medical image data and provide more accurate results than other prior art computational techniques for image processing.

According to various examples, to eliminate processing steps for obtaining annotated training data—e.g., manual annotation by a domain expert—, unsupervised learning may be used to train the convolutional neural network 2020, the first one 2050 and the second one 2070 of the at least one artificial neural network, such as using constraints as disclosed in Celebi, M. Emre, and Kemal Aydin, eds. Unsupervised learning algorithms. Berlin: Springer International Publishing, 2016. Reinforcement learning may be an alternative.

According to various examples, each of the convolutional neural network 2020, the first one 2050 and the second one 2070 of the at least one artificial neural network may be trained using different training techniques, respectively. For example, the convolutional neural network 2020, the first one 2050 and the second one 2070 of the at least one artificial neural network may be respectively trained by using supervised learning, unsupervised learning, and semi-supervised learning.

Next, aspects with respect to a processing workflow to determine at least one characteristic of a rotator cuff will be explained in connection with FIG. 3 and FIG. 4. Specifically, the processing workflows can implement the processing discussed above in connection with FIG. 2. The system 2000 can implement the processing workflows discussed in connection with the processing pipelines 5000 and 6000.

Figure 3:
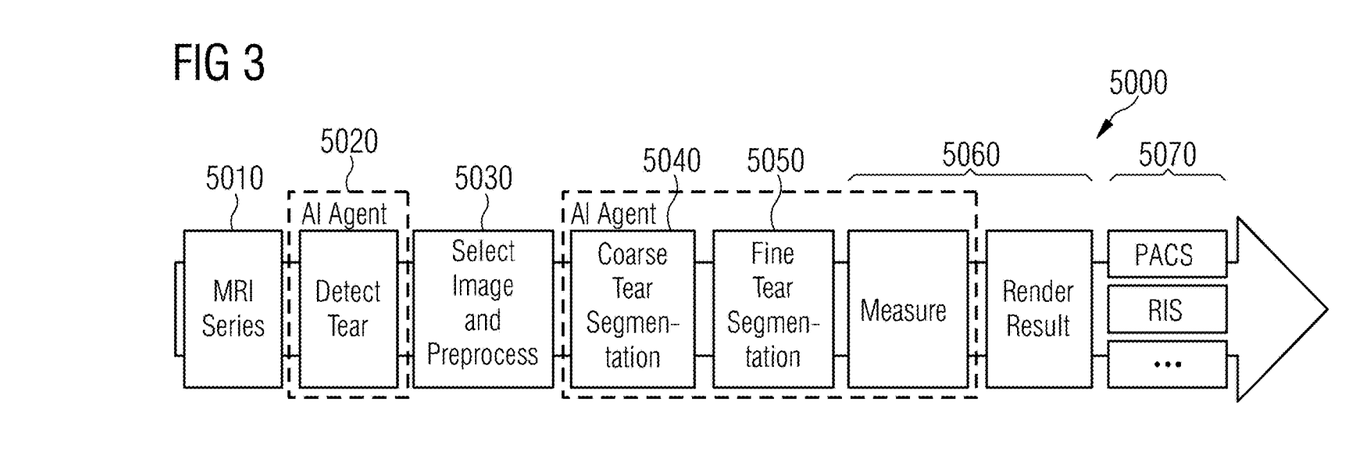
FIG. 3 schematically illustrates a workflow from a clinical perspective.

FIG. 3 is an exemplary clinical processing pipeline 5000 for automatically determining a quantification of at least one characteristic of a rotator cuff tendon tear based on medical imaging data, such as MR imaging data. The quantification of at least one characteristic may comprise a size of the rotator cuff tendon tear (e.g., length, width, thickness) and/or a musculotendinous junction position.

As a general rule, while techniques will be described in connection with determining the quantification of the at least one characteristic, as a general rule, it would be possible to determine a classification of the at least one characteristic. Similar techniques as those described below can be readily applied.

The processing pipeline 5000 may be executed by the system 2000 of FIG. 2 upon loading program code. Details of the processing pipeline 5000 are described below.

At block 5010, an image series (e.g., MRI series) for measurements are defined by the clinical protocol, e.g., the mediolateral dimension of a supraspinatus tendon tear, are measured, e.g., on a coronal oblique fluid-sensitive series. For a selection of an appropriate image series, the system 2000 may use DICOM (Digital Imaging and Communications in Medicine) information. The image series may be loaded from a database. An imaging device may be controlled to acquire and provide the image series. Thereby, one or more medical images are obtained.

At block 5020, presence or absence and/or a type of the tear in the tendon of the rotator cuff is determined using a further AI agent, such as those disclosed in a patent application US 2020/0167911 A1. When performing a medical imaging scan, e.g., an MR scan, the acquired imaging data during the scan, such as image slices, may comprise imaging data depicting both healthy and diseased tissues (e.g., tendon tears). The imaging data depicting diseased tissues are particularly important from a clinical perspective. By using the further AI agent, the imaging data acquired during the scan can be automatically and precisely assigned to at least a first group and a second group respectively corresponding to both the healthy and diseased tissues based on the presence or absence of the tear in the tendon. The following-up processing of the imaging data may focus on the second group, i.e., the imaging data corresponding to the diseased tissues, and thereby consumption of computational resources is reduced. I.e., a pre-filtering can be performed. Further, the further AI agent may determine the type of the tear in the tendon based on the second group of the acquired imaging data. Alternatively, the presence or absence and/or the type of the tear in the tendon may be determined by using a classification algorithm. The classification algorithm is configured to select a class from a list indicating: no tendon tear; a presence of a tendon tear; a partial tear; a low-grade partial tear; a high-grade partial tear; or a full tear.

Block 5020 thus corresponds to pre-processing.

At block 5030, one or more medical images 1000 depicting the rotator cuff are selected based on detection of the presence of the tear and/or the type of the tear. The one or more medical images 1000 may be processed based on a landmark detection algorithm configured to detect a region of interest 1010 in the one or more medical images 1000. Other image processing techniques, such as down-sampling and/or normalizing may be applied before and/or after detecting the ROI 1010 by the landmark detection algorithm.

The pre-processing of blocks 5020 and 5030 can, as a general rule, also be combined in a single pre-processing block.

At block 5040, a coarse tear segmentation is performed by a convolutional neural network, such as 2020 of FIG. 2.

The convolutional neural network 2020 may provide, as an output, a pixel probability map 2030. To get a binary segmentation mask, e.g., a pixel mask 2040, a threshold is applied at, for example, 0.5, on the pixel probability map 2030. The largest connected component is chosen as the final coarse segmentation mask 2040. The segmentation mask 2040 is transferred to the original full resolution images. A bounding box with extra padding in all dimensions may be generated and define the ROI.

At block 5050, fine tear segmentation in the ROI 1010 is performed by the first one 2050 of the at least one artificial neural network and thereby a segmentation 2060 of the ROI 1010 associated with the rotator cuff in the one or more medical images 1000 is determined.

At block 5060, coordinates of the tear, such as respective coordinates of start and end points of the tear, may be extracted from a segmentation mask, e.g., the segmentation 2060, by finding the most distant voxels in the segmentation mask and projecting them into the slice at the center of gravity of the segmentation mask.

At block 5070, the coordinates of the tear are transferred to a target system, such as a PACS workstation, a PACS storage and/or a RIS (Radiological Information System).

The exemplary clinical processing pipeline 5000 facilitates determining quantification of at least one characteristic of a rotator cuff tendon tear, such as a size of the rotator cuff tendon tear (e.g., length, width, thickness) and/or a musculotendinous junction position, based on medical imaging data and thereby significantly improves treatments and/or surgery planning of rotator cuff tears of patients. The exemplary clinical processing pipeline 5000 utilizes AI-based techniques and may significantly reduce the time to determine such characteristics compared to manual approach, and provide consistent and reproducible results which may address both the inter-reader and intra-reader variability in current clinical practice.

Figure 4:
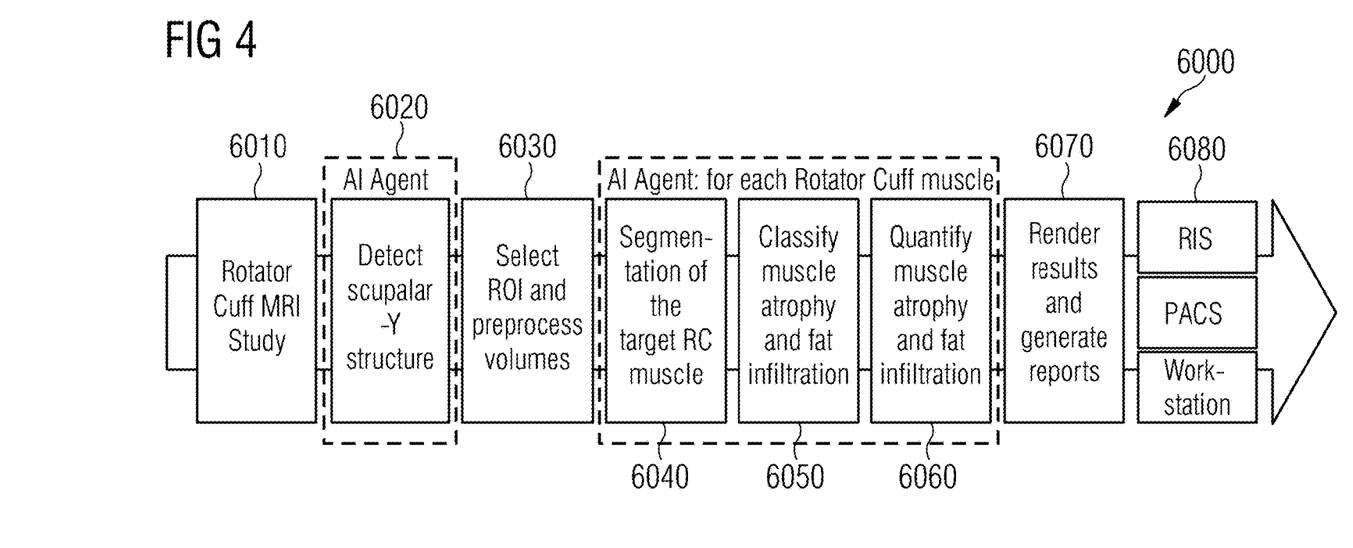
FIG. 4 schematically illustrates another workflow from a clinical perspective.

FIG. 4 is an exemplary clinical processing pipeline 6000 for automatically classifying and quantifying muscle quality of a rotator cuff based on medical imaging data, such as MR imaging data. The muscle quality of a rotator cuff may comprise at least one of a muscle atrophy or a fat infiltration.

The processing pipeline 6000 may be also executed by the system 2000 of FIG. 2 upon loading program code. The processing pipeline 6000 are described below in detail.

At block 6010, an image series (i.e., MRI series) for classifying and quantifying muscle quality of the rotator cuff is obtained, for example, from a database of rotator cuff MRI study. It would be possible that the image series is loaded from an imaging device.

Block 6010 generally corresponds to block 5010.

At block 6020, the scapular-Y structure of the rotator cuff is determined from the scapula bone and a type of a tear in each rotator cuff tendon is classified based on a landmark and using an AI agent. The AI agent may be those disclosed in U.S. Pat. No. 9,792,531 B2 or a patent application US 2020/0167911 A1.

According to various examples, multiple muscles of a muscle structure may be determined to be having muscle quality degradation. For each individual muscle, the following techniques may be applied.

At block 6030, one or more medical images 1000 depicting the rotator cuff is selected based on detection of the presence of the tear and/or the type of the tear to perform muscle quality grading. The one or more medical images 1000 may be processed based on a landmark detection algorithm configured to detect a region of interest 1010 in the one or more medical images 1000. Other image processing techniques, such as down-sampling and/or normalizing and/or cropping may be applied before and/or after detecting the ROI 1010 by the landmark detection algorithm.

Optionally, a coarse tear segmentation is performed by a convolutional neural network, such as 2020 of FIG. 2. The convolutional neural network 2020 may provide, as an output, a pixel probability map 2030. To get a binary segmentation mask, e.g., a pixel mask 2040, a threshold is applied at, for example, 0.5, on the pixel probability map 2030. The largest connected component is chosen as the final coarse segmentation mask 2040. The segmentation mask 2040 is transferred to the original full resolution images. A bounding box with extra padding in all dimensions may be generated and define the ROI.

At block 6040, the muscle structure in the ROI is segmented by, for example, the first one 2050 of the at least one artificial neural network, and optionally based on the segmentation mask 2040, and thereby a segmentation 2060 of the ROI 1010 associated with the rotator cuff in the one or more medical images 1000 is determined.

At block 6050, based on both the segmentation 2060 of the ROI 1010 and the ROI 1010, both the muscle atrophy and the fat infiltration are classified, respectively. Alternatively, the classification of the muscle atrophy and the fat infiltration may be further based on the classification of the tear.

At block 6060, based on both the segmentation 2060 of the ROI 1010 and the ROI 1010, both the muscle atrophy and the fat infiltration are quantified.

At block 6070, both the classification and quantification of the muscle atrophy and the fat infiltration are rendered and optionally an exam report is prepopulated.

At block 6080, both the classification and quantification of the muscle atrophy and the fat infiltration are transferred to a target system, such as a PACS workstation, a PACS storage and/or a RIS (Radiological Information System).

The exemplary clinical processing pipeline 6000 facilitates automate classification and quantification of muscle quality and thereby improves postoperative evaluation of surgeries of rotator cuff tears.

The processing pipelines 5000 and 6000 of FIGS. 3 and 4 are modular. This means that it is not required that all blocks are implemented. Also, further blocks may be implemented. For instance, it may be optional to upload results to the RIS and/or PACS at blocks 5070 and 6080, respectively. The pre-processing at blocks 5020, 5030 and 6020, 6030, respectively may be optional.

Figure 5:
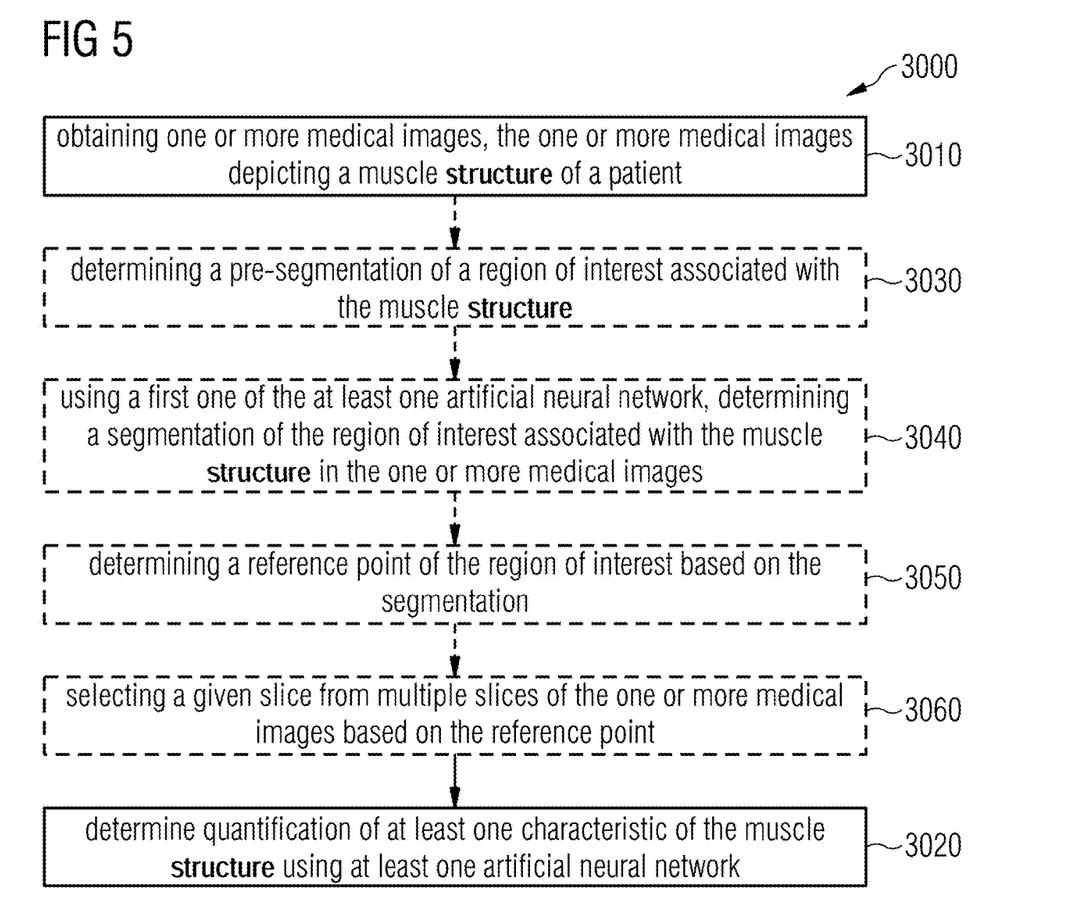
FIG. 5 is a flowchart of a method according to various examples.

FIG. 5 is a flowchart of a method 3000 according to various examples. The method 3000 pertains to determining, by using at least one artificial neural network, such as the at least one artificial neural network of the system 2000, quantification of at least one characteristic of a muscle structure comprising a tendon, such as the rotator cuff, based on one or more medical images 1000 depicting the muscle structure comprising the tendon of a patient.

Optional blocks are labeled with dashed lines.

The method 3000 may be executed by a computer comprising at least one processing unit, or by the system 2000 of FIG. 2 upon loading program code. Details of the method 3000 are described below.

At block 3010, one or more medical images 1000 are obtained, for example by the system 2000 of FIG. 2. The one or more medical images 1000 depicts a muscle structure comprising a tendon of a patient.

The medical images 1000 could be loaded from a picture archiving system (PACS). Block 3010 could include controlling an MRI unit to acquire the images. The medical images 1000 could be loaded from a memory. Alternatively, the medical images 1000 may be received directly from a medical imaging scanner during a scan to perform a real-time determination of the quantification of at least one characteristic of the rotator cuff.

At block 3020, the quantification of at least one characteristic of the muscle structure is determined using at least one artificial neural network. The at least one artificial neural network may be implemented according to the system 2000 of FIG. 2.

Optionally, at block 3010, said obtaining of the one or more medical images 1000 may comprise pre-processing the one or more medical images 1000 based on a landmark detection algorithm configured to detect a region of interest 1010 in the one or more medical images 1000. Such a landmark detection algorithm may be a machine-learning algorithm, see, e.g., U.S. Pat. No. 9,792,531 B2. The region of interest 1010 is associated with the muscle structure. Additionally or alternatively, the image pre-processing techniques described above may be applied before and/or after detecting the ROI 1010 by the landmark detection algorithm.

Optionally, at block 3030, a pre-segmentation of the region of interest associated with the muscle structure is determined, for example by the convolutional neural network 2020 of FIG. 2. The convolutional neural network 2020 may provide, as an output, a pixel probability map 2030. The pre-segmentation may be obtained as a pixel mask 2040 by applying a threshold comparison to probability values of the pixel probability map 2030 and by selecting a largest contiguous area.

The pre-segmentation of the ROI 1010 determined by the convolutional neural network 2020 may be based on a low-resolution version of the ROI 1010 of the one or more medical images 1000, for example obtained by applying down-sampling to the one or more medical images 1000, which may speed up the determination of the pre-segmentation.

Optionally, at block 3040, a segmentation 2060 of the region of interest 1010 associated with the muscle structure in the one or more medical images 1000 is determined using a first one 2050 of the at least one artificial neural network. The segmentation 2060 may be determined based on the pre-segmentation, i.e., the pixel mask 2040, or based on pixel probability map 2030. The segmentation 2060 of a region of interest 1010 determined by the first one 2050 of the at least one artificial neural network may be further based on the one or more medical images 1000 or the ROI 1010.

Additionally or alternatively, the segmentation 2060 may comprise a bounding box which may be determined based on the pixel mask 2040. As a general rule, the bounding box may be the rectangular (in 2-D) or cuboid (in 3-D) of smallest volume that enclosed all relevant features. The determination of the bounding box may comprise determining the location coordinates of the bounding box (e.g. x, y and z coordinates), size parameters of the bounding box (e.g. height, width and depth), and orientation parameters of the bounding box (e.g. angles $\theta x$, $\theta y$ and $\theta z$ which are angles about the x, y and z axes defined with respect to the medical images 1000) for each 2-D medical image or 3-D medical slices. The described coordinates and parameters may be determined such that the bounding box indicates the ROI 1010.

According to various examples, full or original resolution of the ROI 1010 may be selected based on the pre-segmentation, i.e., the pixel mask 2040. Then, the full or original resolution of the ROI 1010 may be fed to the first one 2050 of the at least one artificial neural network to determine the segmentation 2060.

Optionally or alternatively, the method 3000 may, at block 3020, further comprise using at least a second 2070 one of the at least one artificial neural network, determining a value indicative of the quantification of the at least one characteristic based on the segmentation 2060 of the region of interest 1010 and the one or more medical images 1000.

According to various examples, when the at least one characteristic comprises multiple characteristics, the at least one artificial neural network, e.g., the system 2000, may be trained for each individual characteristic separately. I.e., quantification of each individual characteristic may be determined by using the at least one artificial neural network having different parameter values, for example several systems 2000 having the same network architecture but different parameter values.

Optionally or alternatively, when the at least one characteristic comprises multiple characteristics, the quantification of the at least one characteristic may be determined jointly based on the same one of the at least one artificial neural network, e.g., the same system 2000. For example, the at least one artificial neural network may comprise multiple decoder branches 2070a-2070d configured to determine the quantification of the multiple characteristics based on the same input, such as a combination of the segmentation 2060 and the medical images 1000, or in particular, based on a shared set of latent features determined based on the one or more medical images 1000. The multiple decoder branches 2070a-2070d may be parts of the second 2070 one of the at least one artificial neural network.

According to various examples, when the one or more medical images 1000 are or comprise multi-slice images, the method 3000 may further comprise, at block 3050, determining a reference point of the region of interest 1010 based on the segmentation 2060, for example, the location of the detected landmarks may be used as the reference point of the ROI 1010; and at block 3060, selecting a given slice from multiple slices of the one or more medical images 1000 based on the reference point. Then, the quantification of the at least one characteristic may be determined based on an appearance of the muscle structure in the given slice.

According to the disclosure, for example, coordinates of a tear, such as respective coordinates of start and end points of the tear, may be extracted from a segmentation mask, e.g., the segmentation 2060, by finding the most distant voxels in the segmentation mask and projecting them into the slice at the center of gravity of the segmentation mask. Alternatively, the coordinates of the tear may be determined by first determining the center of gravity of the segmentation mask, then selecting the image slice at the center of gravity and measuring the two most distant voxels of the segmentation mask only in the selected image slice. Alternatively or optionally, the coordinates of the tear may be determined based on distances between the two most distant voxels of each slice of the segmentation mask, e.g., selecting the one with the largest length to determine the coordinates, or using a further machine-learning algorithm to determine the best slice to extract the coordinates.

Optionally or alternatively, the at least one artificial neural network may comprise a first artificial neural network configured to determine the presence or absence and/or the type of the tear of the muscle structure. The at least one artificial neural network may further comprise a second artificial neural network configured to determine the classification and optionally the quantification of the muscle atrophy or the fat infiltration. The second artificial neural network may obtain, as an input, an output of the first artificial neural network.

According to various examples, after determining the quantification of the at least one characteristic of the muscle structure, the method 3000 may further comprise at least one of rendering a visualization of the muscle structure including the value of the at least one characteristic, prepopulating an exam report comprising the value of the at least one characteristic, or sending the value of at least one characteristic to the PACS.

According to the disclosure, the method 3000 facilitates automatic and precise determinations of the quantification of at least one characteristic of the muscle structure by using at least one artificial neural network. The method 3000 may significantly reduce the time to determine such quantification of characteristics compared to manual approach, and provide consistent and reproducible results which may address both the inter-reader and intra-reader variability in current clinical practice. Thus, treatments and surgery planning are improved greatly.

Figure 6:
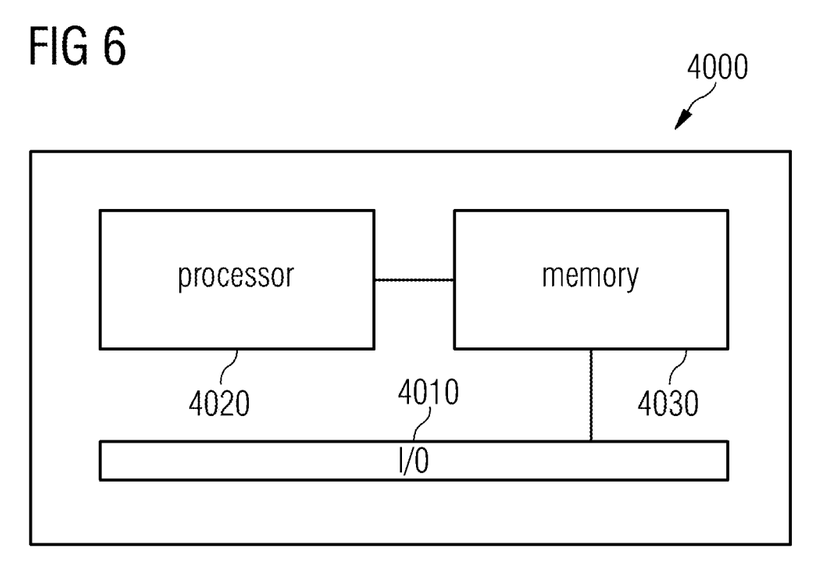
FIG. 6 is a block diagram of a system according to various examples.

FIG. 6 is a block diagram of a system 4000 according to various examples. The system 4000 provides a functionality of determining quantification of at least one characteristic of the muscle structure based on the method 3000.

The system 4000 may comprise at least one processor 4020, at least one memory 4030, and at least one input/output interface 4010. The at least one processor 4020 is configured to load program code from the at least one memory 4030 and execute the program code. Upon executing the program code, the at least one processor 4020 performs the method 3000.

According to the disclosure, a medical imaging scanner, such as a CT scanner, an MRI scanner, an ultrasound scanner, or an x-ray scanner, may comprise the system 4000 of FIG. 6. The medical imaging scanner may determine quantification of at least one characteristic of the muscle structure while performing a scan of a shoulder of a patient.

Alternatively, the system 4000 may be embedded in or connected with the medical imaging scanner and thereby the medical imaging scanner may be also configured to perform the method 3000.

Summarizing, techniques have been described that facilitate determining a quantification and/or classification of at least one characteristic of a muscle structure comprising at least one muscle and at least one tendon, such as the rotator cuff, and thereby significantly improve treatments and/or surgery planning of tears of muscle structures. The at least one characteristic of the muscle structure may be automatically and precisely determined by using artificial intelligence (AI) techniques, such as at least one artificial neural network. Such AI-based techniques may significantly reduce the time to determine such characteristics compared to manual approach, and provide consistent and reproducible results which may address both the inter-reader and intra-reader variability in current clinical practice.

Although the disclosure has been shown and described with respect to certain preferred embodiments, equivalents and modifications will occur to others skilled in the art upon the reading and understanding of the specification. The present disclosure includes all such equivalents and modifications and is limited only by the scope of the appended claims.

The invention claimed is:

1. A computer-implemented method, comprising:
obtaining one or more medical images, the one or more medical images depicting a muscle structure of a patient, wherein the muscle structure comprises at least one muscle and at least one tendon,
determining a pre-segmentation of a region of interest associated with the muscle structure,
using a first one of at least one artificial neural network, determining a segmentation of the region of interest associated with the muscle structure in the one or more medical images, wherein the segmentation is determined based on the pre-segmentation, and
determining a quantification of at least one characteristic of the muscle structure using a second one of the at least one artificial neural network based on the segmentation of the region of interest and the one or more medical images.

2. The computer-implemented method of claim 1, wherein the pre-segmentation is determined using a convolutional neural network, the convolutional neural network providing, as an output, a pixel probability map, wherein the pre-segmentation is obtained as a pixel mask by applying a threshold comparison to probability values of the pixel probability map and selecting a largest contiguous area.

3. The computer-implemented method of claim 2, wherein the segmentation comprises a bounding box which is determined based on the pixel mask.

4. The computer-implemented method of claim 1, wherein determining a quantification of at least one characteristic of the muscle structure using a second one of the at least one artificial neural network based on the segmentation of the region of interest and the one or more medical images comprises:
determining a value indicative of the quantification of the at least one characteristic.

5. The computer-implemented method of claim 1,
wherein the one or more medical images are multi-slice images,
wherein the method further comprises:
determining a reference point of the region of interest based on the segmentation,
selecting a given slice from multiple slices of the one or more medical images based on the reference point,
wherein the quantification of the at least one characteristic is determined based on an appearance of the muscle structure in the given slice.

6. The computer-implemented method of claim 1,
wherein said obtaining of the one or more medical images comprises pre-processing the one or medical images based on a landmark detection algorithm configured to detect a region of interest in the one or more medical images, the region of interest being associated with the muscle structure.

7. The computer-implemented method of claim 1,
wherein the at least one characteristic comprises multiple characteristics,
wherein the second one of the at least one artificial neural network comprises multiple decoder branches configured to determine the quantification of the multiple characteristics based on a shared set of latent features determined based on the one or more medical images.

8. The method of claim 1, wherein the quantification of the at least one characteristic comprises at least one of a length, width, thickness, or musculotendinous junction position of a tendon tear.

9. The method of claim 8, wherein the second one of the at least one artificial neural network comprises a first artificial neural network configured to determine at least one of 1) a presence or absence of the tendon tear in the at least one tendon or 2) a type of the tendon tear in the at least one tendon.

10. The method of claim 9,
wherein the second one of the at least one artificial neural network comprises a second artificial neural network configured to determine the at least one of the length, width, thickness, or the musculotendinous junction position of the tendon tear,
wherein the second artificial neural network obtains, as an input, an output of the first artificial neural network.

11. The method of claim 1, wherein the at least one characteristic comprises a muscle atrophy of the at least one muscle of the muscle structure.

12. The method of claim 11, wherein the second one of the at least one artificial neural network is configured to determine the quantification of the muscle atrophy.

13. The method of claim 1, wherein the at least one characteristic comprises a fat infiltration of the at least one muscle of the muscle structure.

14. The method of claim 13, wherein the second one of the at least one artificial neural network is configured to determine the fat infiltration.

15. The method of claim 1, further comprising:
determining a classification of the at least one characteristic or at least one further characteristic of the muscle structure using the at least one artificial neural network.

16. A system comprising:
at least one processor; and
at least one memory, wherein upon loading and executing program code from the at least one memory, the at least one processor is configured to:
obtain one or more medical images, the one or more medical images depicting a muscle structure of a patient, wherein the muscle structure comprises at least one muscle and at least one tendon,
determine a pre-segmentation of a region of interest associated with the muscle structure,
using a first one of at least one artificial neural network, determine a segmentation of the region of interest associated with the muscle structure in the one or more medical images, wherein the segmentation is determined based on the pre-segmentation, and
determine a quantification of at least one characteristic of the muscle structure using a second one of the at least one artificial neural network based on the segmentation of the region of interest and the one or more medical images.

17. A medical imaging scanner, the medical imaging scanner comprising the system of claim 16.

18. A non-transitory computer readable medium storing computer program instructions, the computer program instructions when executed by a processor cause the processor to perform operations comprising:
obtaining one or more medical images, the one or more medical images depicting a muscle structure of a patient, wherein the muscle structure comprises at least one muscle and at least one tendon,
determining a pre-segmentation of a region of interest associated with the muscle structure,
using a first one of at least one artificial neural network, determining a segmentation of the region of interest associated with the muscle structure in the one or more medical images, wherein the segmentation is determined based on the pre-segmentation, and
determining a quantification of at least one characteristic of the muscle structure using a second one of the at least one artificial neural network based on the segmentation of the region of interest and the one or more medical images.

* * * * *